United States Patent
Armstrong et al.

(10) Patent No.: US 7,760,352 B2
(45) Date of Patent: Jul. 20, 2010

(54) DUAL PULSE SINGLE EVENT RAMAN SPECTROSCOPY

(75) Inventors: Wayne Thomas Armstrong, Placitas, NM (US); Robert Dominic Battis, Mercerville, NJ (US); Robert Michael Jones, Albuquerque, NM (US); Thomas H. Chyba, Tijeras, NM (US); Steven Andrew MacDonald, Arlington, VA (US); Stewart McKechnie, Albuquerque, NM (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 39 days.

(21) Appl. No.: 12/050,590

(22) Filed: Mar. 18, 2008

(65) Prior Publication Data

US 2009/0237648 A1 Sep. 24, 2009

(51) Int. Cl.
G01J 3/44 (2006.01)

(52) U.S. Cl. .................................................... 356/301

(58) Field of Classification Search ............. 356/72–73, 356/301
See application file for complete search history.

(56) References Cited

U.S. PATENT DOCUMENTS

| 4,405,237 | A | 9/1983 | Manuccia et al. |
| 6,788,407 | B1 * | 9/2004 | Higdon et al. ............... 356/301 |
| 7,002,679 | B2 | 2/2006 | Brady et al. |
| 7,177,022 | B2 | 2/2007 | Wang et al. |
| 7,218,440 | B2 | 5/2007 | Green |
| 2005/0168735 | A1 | 8/2005 | Boppart et al. |
| 2005/0248758 | A1 * | 11/2005 | Carron et al. ............... 356/301 |
| 2006/0066848 | A1 | 3/2006 | Frankel |
| 2007/0024964 | A1 | 2/2007 | Ishibashi et al. |
| 2007/0091305 | A1 | 4/2007 | Xie et al. |
| 2007/0103679 | A1 | 5/2007 | Yoo |
| 2007/0215816 | A1 | 9/2007 | Hui et al. |

FOREIGN PATENT DOCUMENTS

| WO | 2007032814 A2 | 3/2007 |
| WO | 2007087315 A2 | 8/2007 |
| WO | 2007123555 A2 | 11/2007 |

OTHER PUBLICATIONS

S.E.J. Bell et al., "Extracting Raman spectra from highly fluorescent samples with "Scissors" (SSRS, Shifted-Subtracted Raman Spectroscopy", Spectroscopy Europe 2002, pp. 17-20.
P. Matousek et al., "Fluorescence background suppression in Raman spectroscopy using combined Kerr gated and shifted excitation Raman difference techniques", Journal of Raman Spectroscopy, 2002, 33: 238-242, John Wiley & Sons, Ltd., www.interscience. wiley.com.
European Search Report (EP09154303), 6 pages, Feb. 19, 2010.

* cited by examiner

*Primary Examiner*—Tarifur Chowdhury
*Assistant Examiner*—Abdullahi Nur
(74) *Attorney, Agent, or Firm*—Edell, Shapiro & Finnan, LLC

(57) ABSTRACT

Systems and methods for performing Raman spectrometry wherein a Raman spectroscopy system is mounted on a vehicle for on the move contaminant analysis. The system is configured to interrogate a target with a laser at a predetermined pulse repetition frequency (PRF), wherein during each PRF cycle, defined as 1/PRF, the laser is dual pulsed at a first wavelength and at a second wavelength. Raman spectra are collected and used to identify the target by matching a Raman signature with a given collected Raman spectra.

20 Claims, 3 Drawing Sheets

SIMULTANEOUS PULSES

SEQUENTIAL PULSES

SEQUENTIAL PULSES

DUAL PULSE SINGLE EVENT RAMAN SPECTROSCOPY

FIELD OF THE INVENTION

Embodiments of the present invention relate to Raman spectrometry sensors, and more particularly to on-the-move Raman sensors having a dual laser pulse single-event capability.

BACKGROUND OF THE INVENTION

The danger of exposure to chemical or biological agents can be severe. Whether a result of unintended release by way of, e.g., an accident, or a result of intentional delivery, it is desirable to quickly and accurately identify (1) the type of agent that has been released and (2) the precise area of contamination. Early and accurate detection of such dangerous substances can be a significant factor in reducing potential casualties and limiting further spreading of the agent by, e.g., wind, human or animal contact, among other transmission mechanisms.

In recent years, there has been an increased interest in developing and deploying sensor technologies to quickly identify unknown substances, contaminants, and agents, even at very low concentrations. Some of these technologies are designed to measure surface-deposited contamination using vehicles and associated test equipment to retrieve a physical sample of the contaminant and then employ extremely cumbersome and time-consuming processes based on a mechanical sampling wheel system to test for agents.

In view of the complexity of such approaches, newer, safer and more reliable technologies have emerged. One such technology is referred to, generally, as "standoff surface detection," and refers to a category of technologies that permit detection of substances without actually having to physically come in contact with the substance or agent of concern. The goal of these detection systems is to provide the capability to detect, identify, locate, quantify, warn, and report chemical or biological threats and thereby give military forces or civilian personnel sufficient early warning to avoid (further) contamination.

An example of a standoff surface detection system is a technology known as Laser Interrogation of Surface Agents (LISA) that has been developed by ITT Industries, Inc. (Wilmington, Del.). In one implementation, LISA uses a laser and associated sensor, attached to a reconnaissance vehicle such as a truck or HMMWV, that looks for chemical agents on the ground (or any surface) using a technique known as Raman Scattering (or Raman Effect, or Raman Spectroscopy analysis), which is an optical property that can be exploited to identify chemical and biological agents. One particular implementation of LISA has a 1.5-meter standoff range and can provide detection on each single laser shot or pulse, at, e.g., 25 pulses per second. This gives personnel manning the vehicle the ability to perform on-the-move, real-time detection of chemical agents on the ground. This on-the-move detection is characterized by single-event detection because each laser shot is a separate event that can produce a detection decision by the sensor and each laser shot is independent of past or future laser shots. The LISA technology also provides the ability to create or generate a position detection map with inputs from, e.g., GPS, with chemical agent contours that build up as detection is taking place.

Standoff biological agent detection is significantly more difficult than chemical detection. Specifically, it is often difficult to discriminate and measure biological agents from naturally occurring background materials. Moreover, real-time detection and measurement of biological agents in the environment can be daunting because of the number of potential agents to be identified, the complex nature of the agents themselves, the countless number of similar microorganisms that are a constant presence in the environment, and the minute quantities of pathogen that can initiate harmful reactions. Potential biological agents can also disguise themselves in benign entities.

In light of these and other obstacles and in furtherance of more accurate contaminant detection capabilities, there is still a need for improvements in stand-off on-the-move detection systems.

SUMMARY OF THE INVENTION

Embodiments of the present invention provide systems and methods for operating, particularly in the field, a Raman spectroscopy device for stand off detection of chemical and biological agents. In one embodiment, there is provided a mobile, stand-off, single-shot, dual pulse, on-the-move Raman spectrometry system that includes a laser module that is configured to generate a first wavelength of energy and a second wavelength of energy from the same laser, wherein the first and second wavelengths of energy are directed along an axis and through free space to a target substance. In a preferred embodiment, the laser produces dual pulses from a single laser aperture (or along a preferred optical path) providing simultaneous or sequential irradiation of the target substance at the first and second wavelengths. This laser producing dual pulses, whether simultaneous or sequential, is hereafter referred to as a dual pulsed laser, dual pulse or dual pulsing. A telescope collects spectral energy patterns that return along the axis and that result from interaction with the first and second wavelengths of energy. An analysis module analyzes the collected spectral energy patterns and matches the same to known spectral energy patterns to identify an unknown substance such as a chemical agent. In a preferred embodiment, the laser module, telescope and analysis module are mounted on a vehicle and operate while the vehicle is in motion.

In one embodiment, the first and second wavelengths of energy are controllable, and may be controlled based on prevailing field conditions. For example, if it is believed that a particular target substance is present and such a target substance has increased response to laser irradiation of a particular wavelength, then the wavelength of the laser light may be changed to that particular wavelength. Likewise, it may be desirable to change, in the field, whether the laser is dual pulsed simultaneously or sequentially. Such a selection may be based on the types of agents being detected, or may also be based on field conditions such as weather, temperature, etc.

In some embodiments the second wavelength of energy is different from the first wavelength of energy.

When the first and the second wavelengths of energy are pulsed sequentially, the temporal spacing, $\Delta T$, is typically less than about 10 µs in order that both laser pulses interrogate the same target species at the prevailing vehicle speed <~60 mph. The 10 µs interval is not a hard limit but depends on the required maximum vehicle speed and the nominal target drop size being interrogated. A temporal spacing of 10 µs used herein as a reasonable upper number, given a maximum vehicle speed of 60 mph and average drop areas of 0.2 $mm^2$.

In accordance with one possible implementation, the laser is an Alexandrite laser configured to provide both the first and the second wavelengths of energy at, respectively, 248 nm and 250 nm, as one example of a wavelength combination.

These and other features of the present invention, along with their attendant advantages, will be more fully appreciated upon a reading of the following detailed description in conjunction with the associated drawings.

DETAILED DESCRIPTION

Figure 1A:
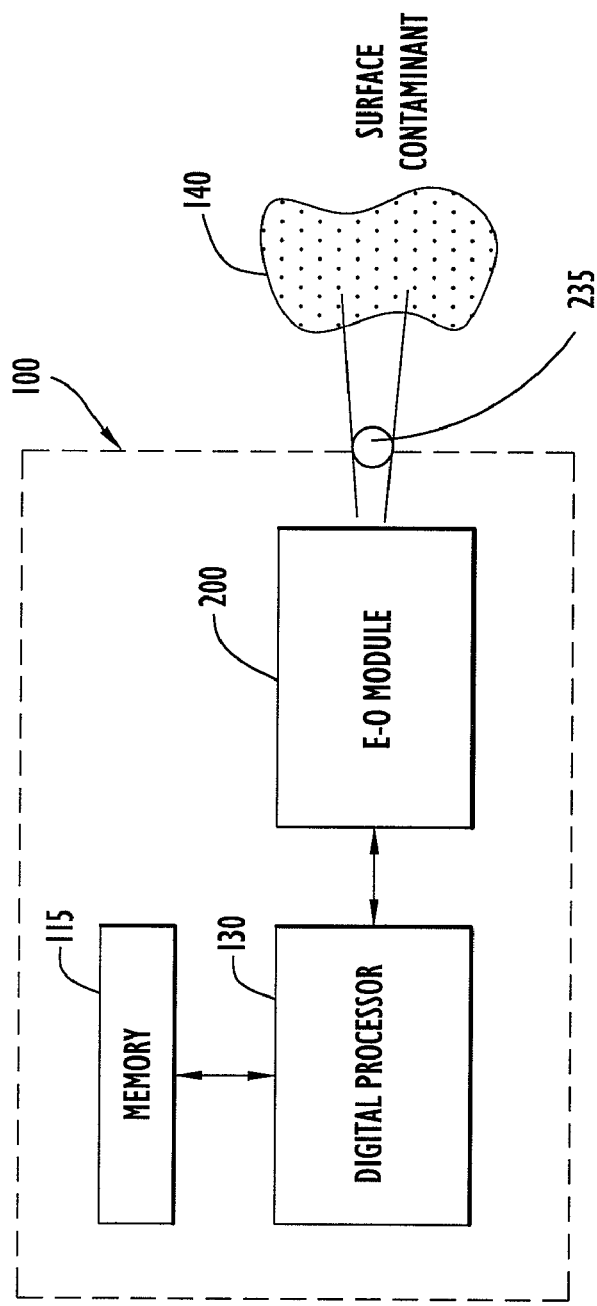
FIG. 1A is a diagram of a Raman spectroscopy system in accordance with an embodiment of the present invention.

FIG. 1A depicts a vehicle mountable Raman spectroscopy system 100 that includes, at a high level, memory 115, processor 130, and an Electronics-Optics (E-O) Module 200 with common system aperture 235, which is described more fully below.

Memory 115 may comprise non-volatile read only memory (ROM) for storing processing instructions (discussed more fully later herein), global variables, initialization variables and routines, and a library of Raman signatures, among other things. Memory 115 may also comprise volatile random access memory (RAM) for storing data (e.g., detected/collected Raman spectral data), sensor status readings, and user input/settings, among other things, including, alternatively, the data described as being stored in ROM. Memory 115 may still further comprise disk drives, flash memory, or any other suitable data storage technology.

Processor 130 is a conventional digital processor or processors suitable to run software routines for, among other things, providing overall system control, including management of inputs and outputs via a user interface (not shown), as well as control signals received from the various components. Processor 130 is preferably also capable of performing the requisite digital signal processing on collected spectral data and comparing the same to a library of Raman signatures stored in memory 115 to identify unknown substances or contaminants. Processor 130 and memory 115 are in communication with one another, as shown, via conventional techniques, e.g., using a control/signal/data bus.

E-O Module 200 (which is described in detail with reference to FIG. 2), is in communication with processor 130 and is arranged to irradiate, using a laser, an unknown substance, such as surface contaminant 140, collect resulting Raman spectral data, and pass the collected data to processor 130 for detailed analysis. The output laser energy and return radiation from the target uses a common system aperture 235, so configured to allow separation of the input and output radiation while co-aligning both. This co-alignment ensures an overlap of laser energy and telescope field of view (FOV) independent of target range. The laser beam propagation cross sectional area is typically about 1 $cm^2$ and the telescope FOV collection area at the target is typically only a little larger in order to maximize SNR. As will be explained more fully below, the laser is arranged to generate dual pulses (separated by time and/or frequency) that are directed to the unknown substance.

Figure 1B:
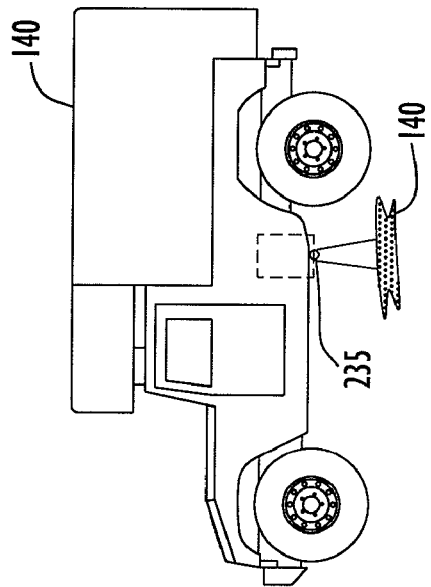
FIG. 1B shows a typical vehicle mounted embodiment of the present invention.

The system 100 (or individual components thereof) is preferably encased in an enclosure (schematically indicated by the broken line in FIG. 1), with a common optical radiation aperture 235. The system 100 is further preferably configured to operate in the field. For example, system 100 may be mounted on a jeep/truck 175 with common radiation aperture 235 of E-O Module 200 directed downward toward the ground, as shown in FIG. 1B. The system may also be configured as a man-transportable device or man-portable device, with the system 100 functionally split into separate parts, e.g., backpack and hand-held parts.

Figure 2:
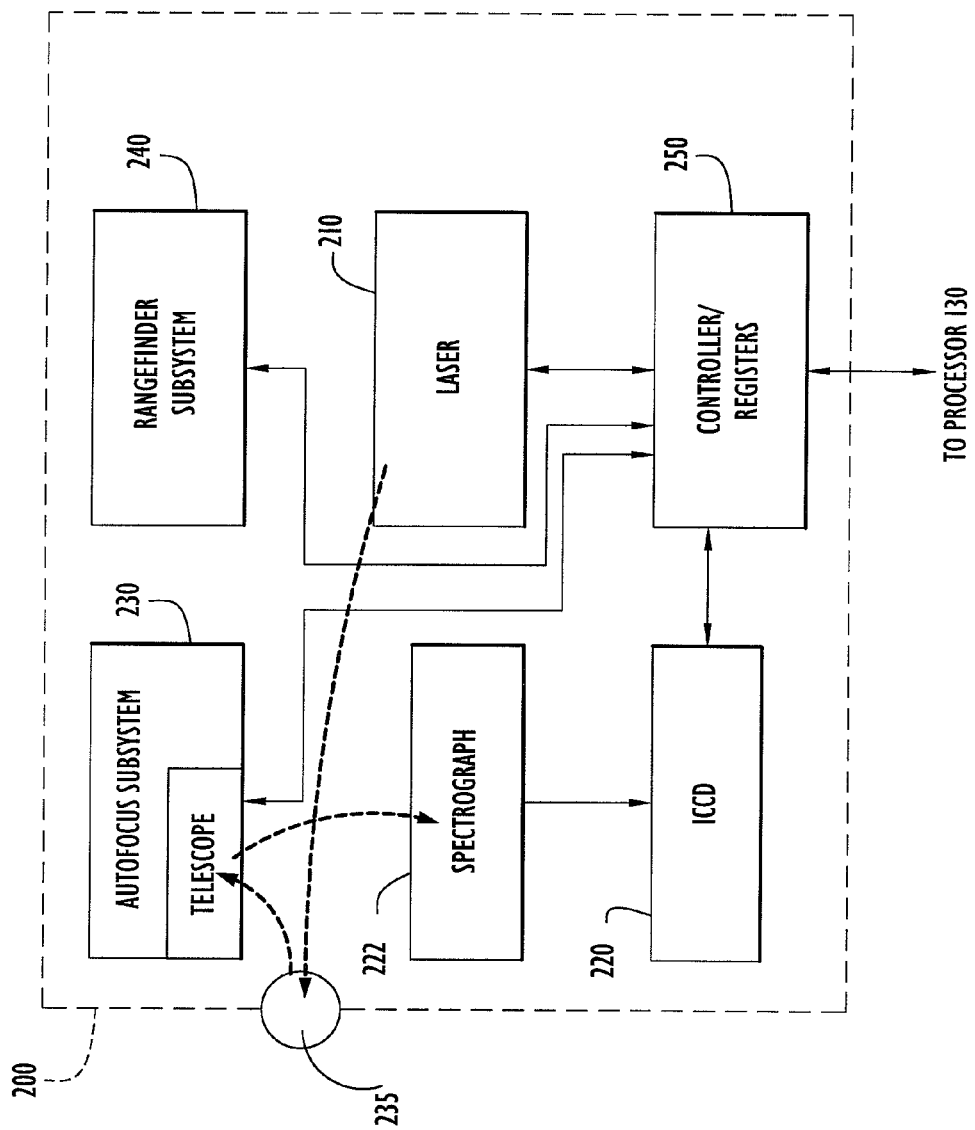
FIG. 2 depicts components of a Raman sensor module in accordance with an embodiment of the present invention.

As shown in FIG. 2, at the heart of the E-O Module 200 is laser 210 that generates a coherent light beam. Laser 210 may produce a beam of light in the ultraviolet (UV) spectrum and be substantially monochromatic (i.e., a single wavelength or limited to a narrow range of wavelengths). Laser 210 preferably produces sufficient light energy such that optical energy returned from an irradiated substance comprises Raman scattered optical energy (spectra) that is analyzed using known spectroscopy techniques. As will be explained in more detail later herein, laser 210 (and/or optics related thereto) is preferably configured to provide dual pulses of energy, either at the same or different wavelength and/or at the same or different instant in time.

Incorporated in laser 210 are various optical or E-O functional elements to provide the desired laser output radiation characteristics, such as single mode, line narrowing and time gating. Also included in E-O Module 200 are a spectrograph 222 and an intensified charge-coupled device (ICCD) 220, the latter serving as a pixilated detector or, generally, "imaging apparatus." As is known in the art, the spectrograph 222 comprises a diffraction grating to disperse scattered radiation (resulting from laser irradiation) onto the ICCD 220. The ICCD 220 may be integrated with the spectrograph 222 as a single unit. Suitable ICCDs that may be used in connection with the system described herein are available from Andor Technology (Belfast, Northern Ireland).

Still with reference to FIG. 2, E-O Module 200 may comprise an Autofocus subsystem 230 and Rangefinding subsystem 240. The ability to focus collection optics, such as a telescope 232 that passes light to the spectrograph/ICCD 222/220), allows for the collection of Raman spectra from a "standoff" distance. While the adjustment of the standoff distance is not required, the measurement process is enhanced by providing this adjustability since the sensor has a limited depth of field for a given standoff range. Focusing may be accomplished by moving, via suitable actuators (motors, gears, etc.), e.g., an optical element(s) of the telescope 232. Such systems are well-known in the art. Focusing may also preferably be performed manually, although automated focusing is preferable.

Rangefinding subsystem 240 provides information regarding the range or distance of an object or unknown substance of interest. This information may be helpful for an Autofocus process, and to improve Raman signal strength of the unknown substance for spectral analysis.

Controller/registers module 250 may be provided in an embodiment to provide electrical communication with components in the E-O Module 200. Controller/registers module 250 may pass commands initiated from processor 130 to one or more components, and may further pass information from any one of the components back to processor 130. Controller/registers module 250 may also buffer information that is received from outputs of associated respective components, thereby realizing a more distributed overall system. Controller/registers module 250 could be incorporated directly into processor 130 (in conjunction with memory 115) such that the several components of the E-O Module 200 are directly connected to the processor 130 without any intervening devices. In this latter case, I/O electronics are part of the Digital Processor 130, which performs the interface function of the separate Controller/registers module 250.

In operation, the laser 210 is pulsed at a predetermined pulse repetition frequency (PRF), e.g., 25 Hz. During each PRF period, or single event period, i.e., 1/PRF, Raman spectra are collected and processed using known methods. In accordance with embodiments of the present invention, instead of pulsing the laser only a single time to produce a single output during each PRF cycle, the laser is configured to provide a dual pulse capability during each PRF cycle. This dual laser output in each PRF cycle may be accomplished in various ways using known methods, depending on the desired simultaneous or sequential output characteristics sought and application specific requirements, such as laser energy and laser pulse width on target and the threshold for laser induced breakdown (LIB) of the target chemicals being irradiated.

Dual pulsing creates different or enhanced Raman signatures that are then processed to improve detection probability ("DP") beyond that which is possible using only a single laser pulse. The technique creates two coincident laser pulses or two pulses temporally spaced so as to interrogate the same small target (defined as a target whose dimension is comparable to the telescope FOV dimension) during the same laser PRF cycle, and do this from a moving vehicle or platform.

Identification of a chemical or biological material based upon its Raman signature typically involves comparison of an unknown signature to a library of known signatures. Various data processing and comparison techniques can be used to assist in identification. The amount of signal relative to noise, or signal to noise ratio (SNR) in the unknown signature will give rise to a limitation on the ability to identify the presence of a chemical or biological material. Various physical and operational parameters are known to influence the SNR of Raman signatures and generally one trades time, energy, spectral resolution or efficiency for SNR. In many applications, a longer sampling time via extending exposure times or multiple sequential samplings are typical operation changes that increase SNR. In the case of single event on-the-move detection, which is a primary application of this invention, improving SNR by extending exposure times or multiple sequential samplings is not possible due to the relative motion between detection system and target. Single event Raman signatures collected from dual or multiple pulses of laser light, either temporally spaced or energy spaced, can be data processed to enhance the SNR, circumventing the need to increase sampling times.

Multiple laser pulses spaced in frequency will create multiple Raman signatures overlapped and offset by the difference in laser frequencies. Data extraction techniques, such as component analysis, applied to multiple offset copies of the collected signature can extract the common responses, i.e., the Raman Signature, while leaving the uncommon responses, i.e., fluorescence and noise. Additional spectroscopic analysis techniques can be applied to the recorded signatures. The improvement in SNR is dependent on the relative magnitudes of different sources of noise, and hardware configuration.

Laser

Not all lasers can be dual pulsed. For example, conventional small excimer lasers are very difficult to dual pulse due to the gas life time, especially at different frequencies. On the other hand, an Alexandrite laser, available from Laser Energetics (Mercerville, N.J.) may be dual pulsed in accordance with embodiments of the present invention. Dual pulsing a laser can be achieved in several conventional ways depending on whether the ultraviolet ("UV") outputs are provided at the same time or separated in both space and time. More specifically, the laser may be configured to have extra-cavity frequency conversion using conventional techniques, wherein there is provided a fundamental alexandrite frequency from the tuned cavity, resulting from flash lamp or diode pumping, followed by frequency tripling using a conventional optical filter or frequency selection optical component, such as a birefringent tuner (BRT) or etalon, and non-linear optical crystals. In one embodiment, dual time separated outputs may be provided by splitting the fundamental cavity beam extra-cavity, adding a delay line in one path and creating two frequency conversion channels, In another embodiment, dual space separated outputs may be provided using conventional techniques by creating two tuned cavities, pumped by a single diode pumping source, with one beam path configured for 744 nm emission (which frequency triples to 248 nm), and the other configured for 750 nm (which frequency triples to 250 nm). These two beam paths contain the appropriate crystals and optical components to provide dual UV wavelength outputs simultaneously using one laser, but with half the power in each UV output, compared to a single channel architecture using the same pump power. With this configuration it is possible to increase the pump power without exceeding the cavity damage threshold, thereby increasing the UV outputs to >½ the energy of a single channel architecture.

For non-simultaneous (i.e. sequential) operation, UV outputs may be provided by, e.g., green pumping twice with a fixed time offset.

Notably, the Alexandrite laser is not necessarily limited to only two UV outputs; the laser, in fact, may be configured to produce many more than two outputs, with a concomitant increase in laser cavity/pump complexity and size. The following discussion is in terms of two UV outputs but it is understood that this, in practical terms, can be expanded to three or four or more outputs.

Dual laser pulsing in accordance with embodiments of the present invention can take several forms. Discussed herein are:

1) Simultaneous Laser Pulses at Different Wavelengths;
2) Sequential Laser Pulses at the Same Wavelength;
3) Sequential Laser Pulses at Different Wavelengths; and
4) Dual Channel Sequential Laser Pulses at Different Wavelengths Each of the foregoing approaches and related sub-approaches are discussed below.

1) Simultaneous Laser Pulses at Different Wavelengths

Figure 3:
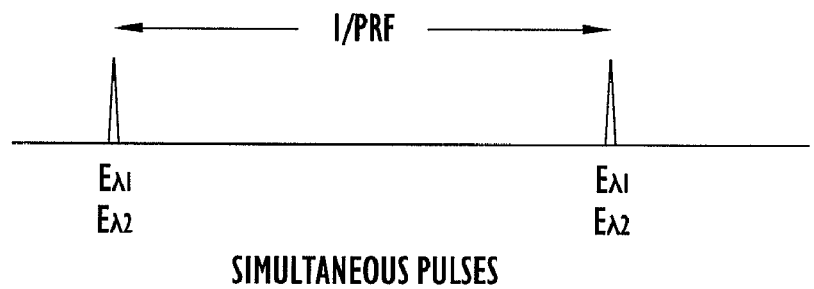
FIGS. 3-5 show laser dual pulsing timing scenarios in accordance with embodiments of the present invention.

In this embodiment, dual UV energy pulses are output from the laser in each PRF cycle, as shown in FIG. 3. Each pulse is at a different wavelength, e.g., 248 nm and 250 nm. This UV excitation produces one Raman signature per PRF cycle containing twice the number of Raman peaks as a single pulse system, but with the same background fluorescence of a single pulse system. It is noted that consideration is preferably given to the two wavelengths selected based upon the desired Raman shift spectrum to collect, and the capabilities of the hardware, i.e., edge filters for Rayleigh rejection.

Since the pulses $E_{\lambda 1}$ and $E_{\lambda 2}$ occur simultaneously the total energy must be limited to an optimized single pulse case to avoid Laser Induced Breakdown (LIB). This means that the respective power of $E_{\lambda 1}$ and $E_{\lambda 2}$ is notionally half of a single pulse $E_\lambda$ for identical laser pulse widths. Consequently, the SNR of individual Raman peaks is half that of a single pulse system, provided that the dominant noise sources do not scale with energy. Given the complexities of various noise sources, it is believed that the SNR of any single Raman peak could scale by factors of ~0.3 to ~0.7. After data processing dual pulsed Raman signatures, the SNR of an extracted correlated Raman signatures are expected to increase to above that of a single pulse. Probability of detection (PD) may increase even without an extraction technique as long as the library signatures are dual pulsed as well. Correlation of twice the Raman spectral information from $E_{\lambda,1}$ and $E_{\lambda,2}$ may also yield a benefit in PD depending upon the comparison algorithms.

In the linear response limit, it is generally true that the background fluorescence will be less than or equal to that observed from a single pulse system.

In circumstances where two temporally and spatially coincident beams interact upon a sample, if sufficient fluence is present, then there exists the necessary circumstances for provoking non-linear $3^{rd}$-order phenomena parametric $2^{nd}$-order processes (in particular those associated with materials interfaces), and bi-linear processes (i.e., pump-probe phenomena), among other phenomena could also occur. Specifically, it is possible that if the wavelength difference, $\Delta\lambda$, is resonant with a Raman vibration then a stimulated response could dominate the spectral return. This has both good and bad implications. On the positive side, a stimulated scattering process is coherent and consequently highly localized in space thereby affording dramatic improvements in collection efficiency. On the other hand, a possible significant downside to this two coincident-beam approach is that all normal spontaneous Raman could be lost; Raman gain would be stolen by the resonant band according to the Planck-Einstein relation, $hc/\Delta\lambda = v_{vib}$, where $v_{vib}$ is the frequency for some Raman active vibrational mode of the interrogated system which includes the target sample and background matrix. Yet another driven process that could be observed with simultaneous dual pulsing could be stimulated emission (fluorescence) if the longer wavelength pulse resides within the emission band of the fluorophore. On the other hand, existing signal processing techniques utilizing filtering/shifting and spectral subtraction can effectively reduce any existing background fluorescence with concomitant increases in Raman band SNR.

Another potential complication owes to pump-probe effects, with the possibility of anomalous spectral signatures. Unfortunately, such behavior is highly dependent upon the photophysics and chemical dynamics of the samples in question, and would require theoretical modeling and/or experimentation to address their significance.

In summary, simultaneous dual pulsing of laser 210 at different wavelengths has the potential of enhancing the Raman signature thereby affording improvements in PD and false alarm rate (FAR) over a single pulse system.

2) Sequential Laser Pulses at the Same Wavelength

Figure 4:
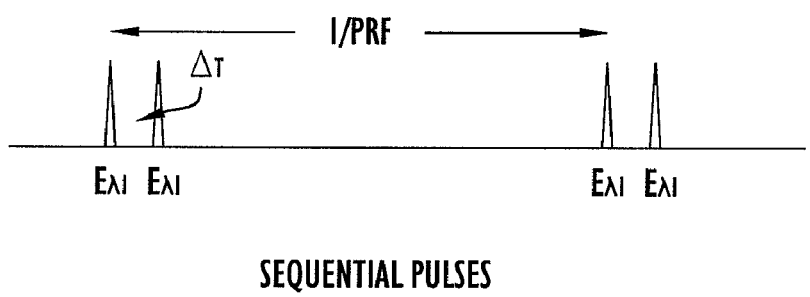

Rather than simultaneous dual pulsing, this embodiment of the present invention provides for sequential or temporally spaced, dual pulsing. In this case, dual UV energy pulses are output from the laser in each PRF cycle, but are offset in time by an interval $\Delta_T$, as shown in FIG. 4. In this particular case, each pulse is at the same wavelength, e.g., 248 nm.

A fundamental premise of this approach (and approach #3 discussed below) and its associated putative benefits, is that of a "fixed" sample, i.e., the second pulse is assumed to interrogate all or most of the same sample volume irradiated by the first pulse. Given the laser fluence levels in question, sample spatial instability is possible due to radiation pressure, thermodynamic (heating) and associated kinetics (heat transfer) effects. As a result, it is possible that the target will move after being hit by the first pulse. Such sample displacements have, in fact, been observed with Thickened Triethylphosphate (TTEPO) (a chemical used as a stimulant) for a pulse time interval $\Delta_T$ of 40 ms. However, it is expected that this phenomena will not result in signal degradation with the second pulse if $\Delta_T$ is kept within about 10 μS. This $\Delta_T$ limit will be referred to as the Pressure Limit in subsequent discussion.

There are two independent signal processing approaches using sequential laser pulses at the same wavelength: Single Mode and Dual Mode. These two approaches will be described independently to avoid confusion:

2A) Single Mode-Sequential Laser Pulses at the Same Wavelength

In Single Mode operation resulting Raman spectra from both laser pulses are processed by the system during the same PRF cycle.

There are limits placed on $\Delta_T$ in addition to the Pressure Limit discussed above. These limits are:

$$\text{LIB lifetime} < \Delta_T < \text{CDD camera aperture time} \qquad \text{Eq. 1}$$

By Eq. 1, the lower limit of $\Delta_T$ must be larger than the LIB lifetime (if LIB were present) to ensure that when the second pulse occurs it does not impart additional fluence sufficient to trigger LIB. When this condition is met, the two laser pulses can be considered as independent events with pulse energies just at or below the LIB threshold.

This two-pulse common wavelength UV excitation of the target produces one Raman signature and if both pulses have the same UV limiting energy (limited by LIB), the SNR of the Raman signature peaks are conditionally doubled while still avoiding LIBs. This scenario improves the SNR by a factor of two in the absence of background fluorescence, and may approach an SNR improvement >2 if significant photo bleaching occurs during the laser pulses. Local heating of the sample generally results in reduced fluorescence resulting from increased excited state deactivation through a collision mediated (temperature dependent) diffusive mechanism.

The net fluorescence yield contributing to the total collected signal will depend upon how $\Delta_T$ compares to the excited state lifetime of the sample absorbers. The number of fluorescent species available in their ground states at the time of arrival of the second laser pulse is entirely dependent upon both the excited state lifetimes and the quantum yield for photolysis. The extent to which photo bleaching occurs impacts the amount of total fluorescence background collected.

Generally speaking, the Single Mode approach requires a simpler optics system compared to the optics system for the Simultaneous Laser Pulses at Different Wavelengths approach.

Other existing signal processing techniques involving filtering and subtraction to reduce the background fluorescence can still be used with this Single Mode approach. Whatever SNR improvements result from filtering and subtraction techniques, the dual pulse signature is an added advantage and furthers the improvement in PD and FAR.

2B) Dual Mode-Sequential Laser Pulses at the Same Wavelength

In Dual Mode operation, only resulting spectra from the second laser pulse are received by the system during the same PRF cycle.

The limits placed on $\Delta_T$ in this case are as follows:

$$\text{Fluorescence lifetime} \ll \Delta_T < \text{CDD camera aperture time} \qquad \text{Eq. 2}$$

Additionally, there is a new requirement imposed on the CCD aperture time as follows:

$$\text{Fluorescence lifetime} \ll \text{CCD aperture opens} < \Delta_T \qquad \text{eq. 3}$$

(where the reference for opening time is the start of the $\Delta_T$ interval)

In Dual Mode, the first UV laser pulse is intended to photo bleach labile fluorescent materials in order that the second pulse returns signals biased toward Raman scattering. The ICCD camera 220 is gated to exclude fluorescence (and Raman) from the first UV pulse. The second UV laser pulse is received and processed by the system with reduced fluorescence background contributions. The energy level in the second pulse is limited by LIBs, but the first laser pulse is not limited by LIBs because no Raman signal is sought. Increasing the energy in the first laser pulse may have the beneficial affect of further improving SNR if significant photo bleaching of the background occurs without concomitant target degradation. Although LIBs is not a concern for the first pulse, the energy nonetheless must be limited to avoid irreversible photo-damage of the target compound as well as to the irrelevant background signals contributing species. Signals derived from the second laser pulse, now with reduced fluorescence contamination, are processed in the usual way. Reduced fluorescence improves the system SNR and therefore PD and FAR.

It is believed that this Dual Mode approach improves PD and FAR compared to the improvements possible using the Simultaneous Laser Pulses at Different Wavelengths approach owing to reductions in background fluorescence and a concomitant increase in the SNR of the Raman signature.

The nature of the samples interrogated, in particular the existence of background fluorescence, will largely dictate whether the Single Mode or Dual Mode approach will yield better PD and FAR. In general, it is believed that improved PD and FAR will result from signatures processed without fluorescence compared to signatures processed with fluorescence and with software mitigation of fluorescence.

Interaction of the target with the first laser pulse may result in some combination of absorption, inelastic scattering, and dielectric heating (in addition to radiation pressure related mechanical phenomena). The other "lossy" (energy) phenomena described will result in a possibly large increase in sample temperature. This increased local non-equilibrium sample temperature may only persist for a finite period of time. The statistical mechanical, bulk thermodynamic, and transfer properties of the sample will cause the heated sample to "relax" back to the equilibrium state existing prior to irradiation (in the absence of photo/chemical reactions). To the extent that the reacquisition of equilibrium is facilitated by mass transfer (rather than by radiation) the detailed molecular composition of the sample volume may change. (In fact, the immediate consequence of localized sample heating would be a transient acoustic, followed by a diffusion limited thermal expansion resulting in a change in molecular density.) Consequently, any benefits derived from this double-pulsing will depend upon these dynamical considerations, which may be sample-dependent.

The molecular consequences of a "hot" sample may be manifested as the redistribution of energy amongst accessible vibronic states of the molecules. If the second pulse arrives in time to interrogate these "hot" species, new spectral signatures can be anticipated. Perhaps the most important of such "hot" species could be the production of anti-Stokes Raman bands, which can be invaluable from a chemical information standpoint.

The laser/optics configuration for this Dual Mode approach is less complex than the laser configuration in the Simultaneous Laser Pulses at Different Wavelengths approach.

The other existing signal processing techniques may still be applied to these Dual Mode spectral data. Whatever SNR improvements result from filtering and subtraction techniques, this Dual Mode approach may potentially provide an added advantage in sample circumstances involving labile fluorescent backgrounds.

3) Sequential Laser Pulses at Different Wavelengths

Figure 5:
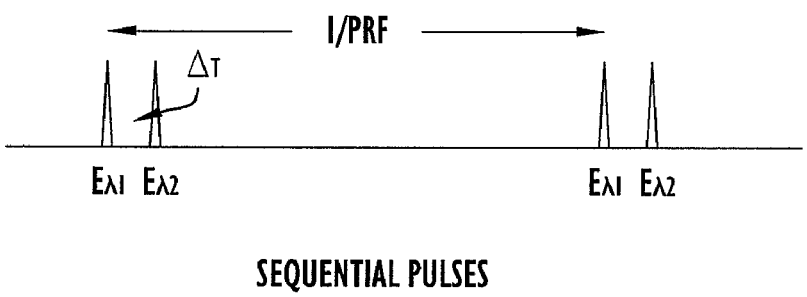

In this third embodiment, dual UV energy pulses are output from the laser in each PRF cycle but offset in time by an interval $\Delta_T$, as shown in FIG. 5. Each pulse is at a different wavelength, e.g., 248 and 250 nm.

The $\Delta_T$ Pressure Limit discussed in Approach #2 (Sequential Laser Pulses at the Same Wavelength) also applies here.

Likewise, there are two independent signal processing approaches using sequential laser pulses at different wavelengths, equivalent to Approach #2 above. These two approaches are described independently below:

3A) Single Mode-Sequential Laser Pulses at Different Wavelengths

In Single Mode operation, resulting spectra from both laser pulses are received by the system during the same PRF cycle.

There are limits placed on $\Delta_T$, as in approach 2A) and these are given in Eq. 1.

This dual pulse UV excitation of the target produces one Raman signature per PRF cycle, but if both pulses have the same UV limiting energy (limited by LIB), the SNR of the Raman signature peaks are conditionally the same as a single pulse case but there is twice the spectral information available to the Raman signature extraction processing.

It is believed that the background fluorescence may be, assuming the absence of stimulated phenomena, less than or equal to that observed using known single pulse systems.

The previous comments pertaining to the loss of spectral information due to Rayleigh rejection concerns also applies here.

In summary, sequentially pulsing the laser at different wavelengths may double the information available to a Raman signature extraction process operating in conjunction with memory 115 and processor 130. Additionally, the Raman peaks are presented with the same SNR as a single pulse system assuming the laser is designed to produce equal energy pulses. The background fluorescence is believed, by virtue of thermal and photolytic affects, to be less than twice that observed with conventional single pulse systems. With the forgoing in mind, the net improvements in PD and FAR over a single pulse system may be significant.

The laser used in this Single Mode approach may have the same complexity as the laser in the Simultaneous Laser Pulses at Different Wavelengths approach.

Other known signal processing techniques utilizing filtering and/or spectral subtraction followed by Raman shift corrections may effectively reduce remaining background fluorescence with concomitant increases in Raman band SNR.

3B) Dual Mode-Sequential Laser Pulses at Different Wavelengths

In this Dual Mode approach, resulting spectra from only the second laser pulse are received by the system during the same PRF cycle. The first laser pulse is intended to photobleach labile fluorescing species as described in approach 2B), the Dual Mode-Sequential Laser Pulses at the Same Wavelength approach.

Since the first pulse is gated out of the system, there may be no practical advantage of this approach over approach 2B), except to add flexibility to a system in being able to switch between modes 3B and 3A. The laser design for this approach is more complex than that required in approach 2B).

4) Dual Channel-Sequential Laser Pulses at Different Wavelengths

In this embodiment, dual UV energy pulses are output from the laser in each PRF cycle and are offset in time by an interval $\Delta_T$, as shown in FIG. 5. Each pulse is at a different wavelength, e.g., 248 nm and 250 nm. This approach requires the same laser as in approach 3A). The main difference between this approach and that of 3A), however, is that each output, $E_{\lambda 1}$ and $E_{\lambda 2}$ is processed by the system using a separate spectrograph/ICCD channel.

Accordingly, this approach allows direct subtraction of the background at the expense of adding another spectrograph channel. The improvements in SNR, PD and FAR are best when compared to all other approaches: background fluorescence is eliminated, SNR is maximized because each laser pulse is at the LIBs energy limit and there is twice the information available for Raman signature processing. From an implementation perspective, however, one must decide whether the improved performance justifies the added expense of the second channel (spectrograph/CCD). One factor that may be considered includes the types of contaminants or agents that are expected to be analyzed. If increased fidelity, on the order provided by the instant embodiment, is believed necessary, then the cost may indeed be justified.

Still another embodiment of the present invention provides for the dynamic control of laser wavelengths. For example, rather than 248 nm and 250 nm, one or both wavelengths could be changed or controlled by tuning laser 210 in an appropriate manner. This may be beneficial depending on the environment in which the system is operating, and/or the types of contaminants that are believed to be present. Moreover, control of the laser frequency may be based on conditions being experienced in the field including weather, temperature or characteristics of a given geographic region. Control may be automatic, manual or a combination thereof.

The systems and methods described herein may be embodied in other specific forms without departing from the spirit or essential characteristics thereof. The foregoing embodiments are therefore to be considered in all respects illustrative and not meant to be limiting.

What is claimed is:

1. A mobile, stand-off, single-event, dual pulse, on-the-move Raman spectrometry system, comprising:
   a laser module that is configured to generate a first wavelength of energy and a second wavelength of energy, wherein the first and second wavelengths of energy are directed, at substantially the same time, along an axis and through free space to a target substance, wherein the first and the second wavelengths of energy are pulsed sequentially with a temporal spacing of $\Delta T$;
   a telescope for collecting a spectral energy pattern that returns along the axis and that results from interaction of the target substance with the first and second wavelengths of energy;
   a charge coupled device for receiving a collected spectral energy pattern from the telescope; and
   an analysis module for analyzing the collected spectral energy pattern and matching the collected spectral energy pattern to a known spectral energy pattern,
   wherein $\Delta T$ is less than about 10 μS, and
   wherein the laser module, telescope and analysis module are mounted on a vehicle and operate while the vehicle is in motion.

2. The system of claim 1, wherein the first and second wavelengths of energy are controllable.

3. The system of claim 2, wherein the first and second wavelengths of energy are controllable based on field conditions.

4. The system of claim 1, wherein the second wavelength of energy is different from the first wavelength of energy.

5. The system of claim 1, wherein the Raman spectrometry system includes an imaging apparatus and $\Delta T$ is set to be consistent with the following equation:

$$\text{LIB lifetime} < \Delta T < \text{aperture time of the imaging apparatus}$$

where LIB is laser induced breakdown.

6. The system of claim 5, wherein the imaging apparatus comprises a charge coupled device (CCD).

7. The system of claim 1, wherein the wavelengths of the first and the second wavelengths of energy are, respectively, 248 nm and 250 nm.

8. The system of claim 1, wherein the laser module comprises a single laser configured to provide both the first and the second wavelengths of energy.

9. The system of claim 1, wherein the first pulse is of sufficient power to photo bleach a background around the target substance.

10. A method for performing Raman spectrometry, comprising:
    operating a vehicle having mounted thereon a Raman spectroscopy system, the Raman spectroscopy system comprising a laser, collection optics and an imaging apparatus;
    interrogating a target with the laser at a predetermined pulse repetition frequency (PRF), wherein during each PRF cycle, defined as 1/PRF, the laser is dual pulsed at different wavelengths sequentially and spaced apart by a time $\Delta T$ that is less than about 10 μs;
    collecting Raman spectra, using the collection optics, during each PRF cycle; and
    identifying the target by matching a Raman signature with a given collected Raman spectra or series of Raman spectra.

11. The method of claim 10, wherein the PRF is about 25 Hz.

12. The method of claim 10, wherein $\Delta T$ is set to be consistent with the following equation:

$$\text{LIB lifetime} < \Delta T < \text{aperture time of the imaging apparatus}$$

where LIB is laser induced breakdown.

13. The method of claim 10, further comprising dynamically controlling at least one of the wavelengths.

14. The method of claim 13, further comprising dynamically controlling the at least one of the wavelengths based on operating or field conditions.

15. The method of claim 10, further comprising photo bleaching a background around the target substance.

16. A method for performing Raman spectrometry, comprising:
    operating a vehicle having mounted thereon a Raman spectroscopy system, the Raman spectroscopy system comprising a laser, collection optics and an imaging apparatus;
    interrogating a target with the laser at a predetermined pulse repetition frequency (PRF), wherein during each PRF cycle, defined as 1/PRF, the laser is dual pulsed sequentially at a first wavelength and at a second wavelength, wherein the second wavelength is different from the first wavelength;
    collecting Raman spectra, using the collection optics, during each PRF cycle by collecting Raman spectra resulting from irradiation of the target by both the first wavelength and the second wavelength; and
    identifying the target by matching a Raman signature with a given collected Raman spectra, wherein a difference in time, ΔT, between the sequentially dual pulsed first wavelength and the second wavelength is less than about 10 μs.

17. The method of claim 16, wherein ΔT is set to be consistent with the following equation:

LIB lifetime<ΔT<aperture time of the imaging apparatus where LIB is laser induced breakdown.

18. The method of claim 16, further comprising dynamically controlling at least one of the first wavelength and the second wavelength.

19. The method of claim 18, further comprising dynamically controlling the at least one of the first wavelength and the second wavelength based on operating or field conditions.

20. The method of claim 16, further comprising photo bleaching a background around the target substance.

* * * * *

UNITED STATES PATENT AND TRADEMARK OFFICE
CERTIFICATE OF CORRECTION

PATENT NO.        : 7,760,352 B2
APPLICATION NO.   : 12/050590
DATED             : July 20, 2010
INVENTOR(S)       : Wayne T. Armstrong It is certified that error appears in the above-identified patent and that said Letters Patent is hereby corrected as shown below:

Column 7, line 63, replace "as a stimulant" with -- as a simulant --.

Signed and Sealed this

Seventh Day of September, 2010

David J. Kappos
*Director of the United States Patent and Trademark Office*